United States Patent [19]
Watkins

[11] Patent Number: 6,013,915
[45] Date of Patent: Jan. 11, 2000

[54] PROCESS CONTROL BY TRANSIENT THERMOGRAPHY

[75] Inventor: Michael Watkins, Chester, Va.

[73] Assignee: Philip Morris Incorporated, New York, N.Y.

[21] Appl. No.: 09/021,224

[22] Filed: Feb. 10, 1998

[51] Int. Cl.[7] .............................. G01J 5/02; G01N 25/72
[52] U.S. Cl. ................... 250/341.1; 250/341.6; 250/341.7; 250/341.8; 250/359.1; 374/5
[58] Field of Search .............................. 374/5; 250/341.1, 250/341.7, 341.8, 359.1, 338.1, 341.6

[56] References Cited

U.S. PATENT DOCUMENTS

| | | | |
|---|---|---|---|
| 5,032,727 | 7/1991 | Cox, Jr. et al. | 250/330 |
| 5,075,552 | 12/1991 | McClelland et al. | 250/341.6 |
| 5,111,048 | 5/1992 | Devitt et al. | 250/342 |
| 5,305,893 | 4/1994 | Hereford | 209/577 |
| 5,444,241 | 8/1995 | Del Grande et al. | 250/253 |
| 5,582,485 | 12/1996 | Lesniak | 374/5 |
| 5,659,624 | 8/1997 | Fazzari et al. | 382/110 |
| 5,705,821 | 1/1998 | Barton et al. | 250/458.1 |
| 5,711,603 | 1/1998 | Ringermacher et al. | 374/5 |
| 5,827,549 | 10/1998 | Rancich et al. | 425/145 |
| 5,845,002 | 12/1998 | Heck et al. | 382/110 |

*Primary Examiner*—Constantine Hannaher
*Assistant Examiner*—Albert Gagliardi
*Attorney, Agent, or Firm*—Charles E.B. Glenn; Kevin B. Osborne; Clinton H. Hallman, Jr.

[57] ABSTRACT

A method and apparatus for detecting, locating, isolating and controlling variations in the manufacturing process by transient thermography. A heat source imparts heat to a surface which is radiated in the infrared region. Infrared sensors are coupled to a processor which tracks the physical characteristics of the sample, and provides feedback to a central process controller to make adjustments to the manufacturing process.

15 Claims, 12 Drawing Sheets

PROCESS CONTROL BY TRANSIENT THERMOGRAPHY

1. BACKGROUND OF THE INVENTION

A. Field of the Invention

The present invention relates to an apparatus, system and method for the production of high-quality materials. More specifically, the present invention relates to the thermal inspection of materials, location of defects in those materials, and providing of feedback into a processing control to identify, reduce, and remove the incidences of defect production in the material.

B. Description of the Prior Art

Thermography is generally known. It is used, e.g., in probing aircraft surfaces and other materials for hidden cracks and flaws.

U.S. Pat. No. 5,711,603 discloses a transient depth thermography technique for the nondestructive testing of objects. The method includes steps of heating the surface of an object, recording pixel intensity for each pixel in a heated surface, and determining pixel contrast from pixel intensity. The method monitors the pixel contrast over successive images to determine the location of a flaw within an object and the surface can be depicted on a print which correlates the flaws with their depth coded by color.

U.S. Pat. No. 5,705,821 discloses a method and apparatus for checking IC chips for defects by scanning fluorescent microthermal imaging. The method uses a scanned and focused laser beam to excite a thin fluorescent film disposed on the surface of an integrated circuit chip. Localized heating associated with IC chip defects is observed by collecting fluorescent radiation from the film and forming a thermal map.

U.S. Pat. No. 5,582,485 discloses a method of analyzing structures by time-varying thermal signals. A projector projects a moving pattern of heat onto a test object, and an infrared camera insensitive to the projected wavelength detects emitted heat from the object. Variances in the pattern are caused by heat buildup by resistance to downward and lateral flows of heat energy, and thus may detect cracks and debonding simultaneously.

U.S. Pat. No. 5,444,241 discloses a dual-band infrared imaging method. Computerized tomography images the structure using infrared. A structure to be imaged is heated by at least two different wavelengths of infrared radiation, images are sequentially obtained, and the images are utilized to determine whether a flaw is present.

U.S. Pat. No. 5,032,727 discloses the detection of defects in manufactured products by thermal ratio analysis, which is said to involve the ratio s of thermal data and their analysis including statistical analysis. Also disclosed is image enhancement and the rejection of known artifacts.

II. SUMMARY OF THE INVENTION

To ensure the quality of a processed material, the present invention contemplates utilizing the anisotropic heat flow properties of an irregular manufactured material to detect and control variations in the manufacturing process. Additionally, the present invention contemplates the supplying of additional useful processing data by decoupling certain measurements, e.g. thickness and density, to enable optimized process control. Finally, the locating and isolating of defective material in a process stream assures a high quality output.

III. OBJECTS OF THE INVENTION

It is an object of the present invention to provide reliably high quality materials from a manufacturing process.

It is an object of the present invention to provide a defect detection system which will provide indication of defects in partially processed materials before their processing is complete to save waste.

It is an object of the present invention to provide a feedback loop system for controlling a manufacturing process on line to reduce the amount of waste material produced.

It is an object of the present invention to provide on-line component control for a manufacturing process via a feedback system to allow for real time adjustment of the process.

It is a further object of the present invention to provide images of the material manufactured indicating the presence or absence of flaws as a quality control checkpoint.

It is an additional object of the present invention to provide individual datum on physical characteristics of a material instead of coupled data from a plurality of characteristics.

IV. BRIEF DESCRIPTION OF THE DRAWINGS

V. DETAILED DESCRIPTION

The apparatus and method according to the present invention may perhaps be best understood with reference to a specific end use—e.g. the manufacture of alloys by various processes. The following discussion is for illustration and should not be construed as a limitation to the scope of the invention.

Alloy manufacture requires numerous specific processing steps and discrete component additions to result in an alloy having precisely calibrated properties. Even minor deviations from preselected characteristics of processing may result in flawed or unusable materials. The alloy can be characterized by uniformity, particle size, thickness, and various other parameters which will affect the final product characteristics. Of particular importance, processing of alloy materials when they are in their earliest formative steps, e.g. as a so-called "green sheet" requires a particularly noninvasive type of analysis.

For example, alloys used as electrical resistance heating elements require specific resistances to achieve a certain temperature while drawing a certain current. The alloys must also resist a tendency to creep, oxidize, or otherwise degrade over extended cycling through high temperatures. These characteristics are frequently tied to the alloy components, but it should be noted that they are also directly related to various processing steps.

It would be desirable to detect problems arising during the processing of the materials in a manufacturing process and rejection of those materials with concomitant correction of the manufacturing process to reduce waste and excess costs associated therewith. It is far cheaper to detect a flawed batch of materials than to replace a heater in e.g., a toaster, electrical smoking system, a filament in a light bulb, or the like. It is also desirable to conduct such an analysis with a noninvasive procedure, e.g. one of the present invention which causes minimal temperature changes, on the order of magnitude of 1–10 degrees, especially 2–5 degrees C°.

Figure 1:
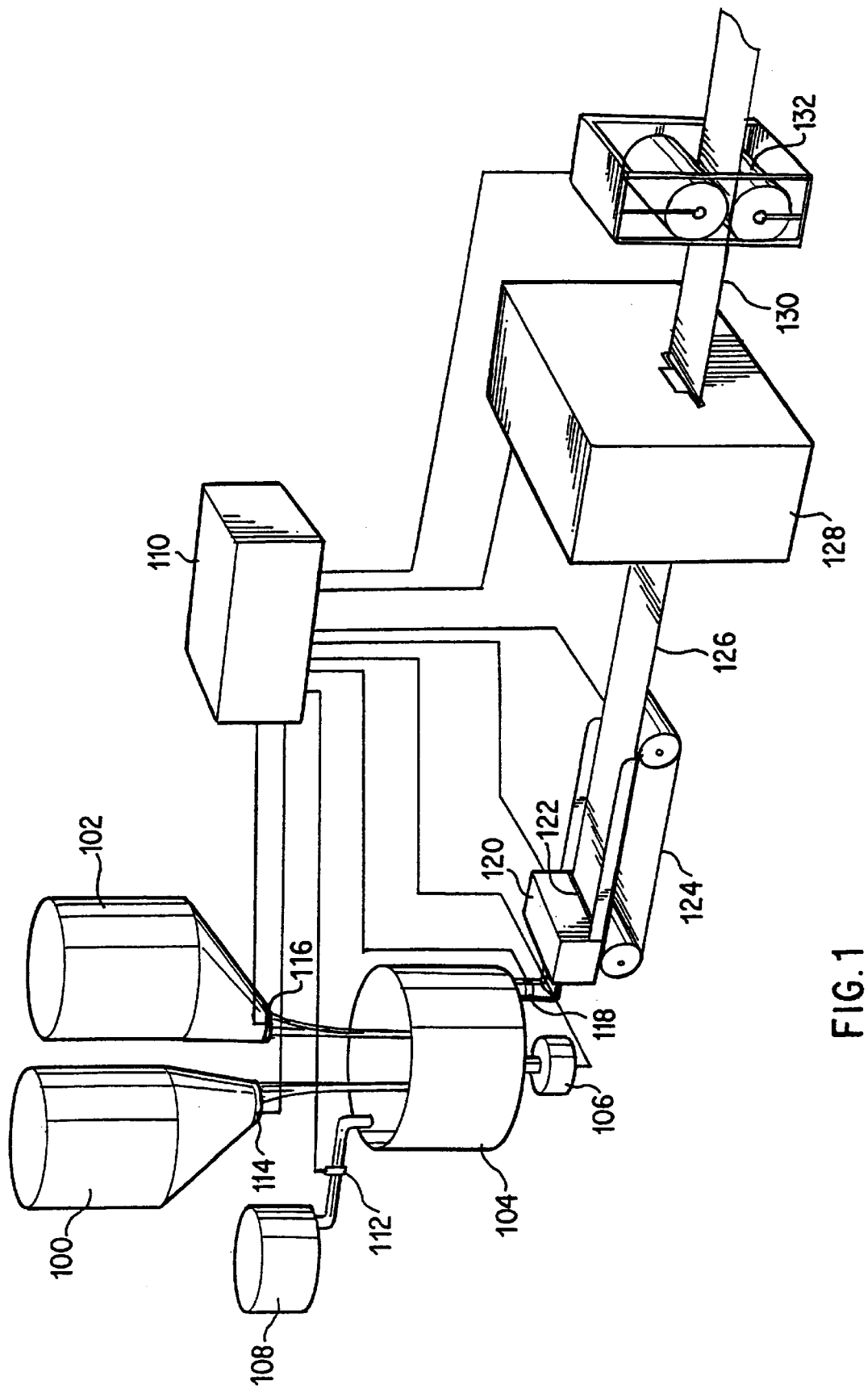
FIG. 1 is a perspective view of a production line for the manufacture of an alloy according to the present invention.

Turning now to FIG. 1, where is illustrated one method of manufacturing an alloy, we can see the various components of the process. Alloy raw materials, which may be in powdered form, are contained in bins 100 and 102. Any number of bins may be added as appropriate for the alloy content. Indeed, some of the bins may contain premixed powders or the like depending on the specific alloy formulation chosen for manufacture. By way of example, let us assume bin 100 contains iron powder and bin 102 contains aluminum for use in a tape casting process. Other processes, such as cold-rolling of elemental powders, may be used and chosen by one of skill in the art, but for ease of discussion we will focus on one process.

Each bin empties into mixing vessel 104 which is churned or mixed by motor 106 connected to mixing blades or other means (not shown). Bin 108 contains a binder system. Bin 108 empties into mixing vessel 104 as well. Controller 110 determines the rates of flow of the component materials, and thus the ultimate alloy composition, by sending signals to valves 112, 114, and 116 to control their rates of flow into the mixture. Such control may also be maintained by pumps, conveyors, etc.

The mixture exits mixing vessel 104 and passes through valve 118 into headbox 120. Headbox 120 has an orifice 122 proximate to a moving endless conveyor belt 124. Orifice 122 is height adjustable. The mixture emerges, e.g. by extrusion, from orifice 122 onto conveyor 124 to form a tape casting 126. The tape casting passes through a chamber 128 which can apply heat (e.g. flash drying) or vacuum for removal of binder in varying amounts.

Such drying forms a "green sheet" 130. The green sheet 130 may then be processed by rolling in a rolling mill 132. Optionally, further steps such as annealing and additional hot or cold working, e.g. extrusion, rolling, drawing, etc. may be conducted upon the green sheet.

It may be seen that careful process control is necessary throughout the above process to yield an end product with appropriate thickness, constituents, consistency, particle sizes, and the like.

The green sheet, after it has stabilized at least in part, may be inspected at various locations along the path of processing. For example, if the casting machine has a sufficiently long conveyor such that the sheet is self-supporting, an inspection station may be established prior to debindering and flash drying. An inspection station may also be established after the drying/debindering step, and after the rolling step.

Figure 2:
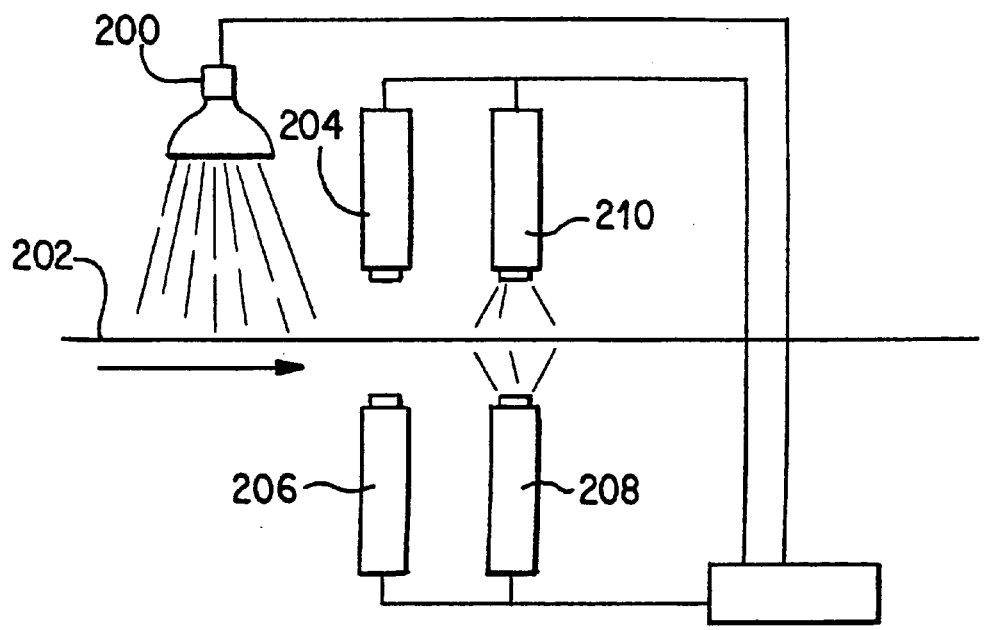
FIG. 2 is a side view of a transient thermography inspection system according to the present invention.

An exemplary generic inspection station is as illustrated in FIG. 2. Heat source 200 throws radiation upon surface 202. The radiation may be visible, ultraviolet, infrared, or even magnetic induction. A particularly preferred embodiment includes monochromatic, e.g. laser, light focused in a band, to a point, or other spatial pattern. Especially preferred embodiments include temporal modulation, e.g. a pulsed source with pulses occurring in a frequency of from 1 to 500 Hz. Especially suitable for this invention is from 50 to 150 Hz, more especially about 100 Hz.

A suitable lamp is, e.g. a Balcar 6.4 kJ xenon flash lamp with associated power supply manufactured by Balcar, Inc., France. A suitable laser is a Magnum Diode Laser (4 watts) with associated optics (line, spot, grid optic generator) manufactured by Lasiris, Inc. Quebec, Canada.

The surface is in one embodiment traveling in the direction of the arrow in FIG. 2. Such a process would be a continuous inspection process. The practice of the invention is equally appropriate for batch processes, even though the benefits of on-line correction are reduced to a batch-wise correction.

Although not being bound by theory, it is believed that when the surface is heated it emits infrared radiation in a particular pattern as it cools. The surface travels between sensors 204, 206, 208 and 210. These sensors may be line scan IR cameras, CCD IR cameras which image defined fields, or the like, so long as they have the capability of capturing the pattern of heat radiating from the surface of the alloy. Sensors 204 and 210 detect the reflected heat, while sensors 206 and 208 detect the transmitted heat.

Suitable cameras include infrared two dimensional arrays such as the ThermaCAM SC1000™ camera manufactured by Inframetrics, Inc. North Billerica, Mass.; the Prisim DS™ camera, manufactured by FLIR Systems, Inc., of Portland, Oreg.; and the Radiance™ camera, manufactured by Raytheon Amber, Inc., Goleta, Calif.

The heat radiating from the surface 202 changes over time as the surface travels in the direction of the arrow. The images captured by cameras 204 and 206 differ in time from those captured by cameras 208 and 210, therefore the pattern of cooling may yield additional information not found by a singular image. Image analysis software will differentiate between the cooling temperatures over time and deeper flaws will become visible or otherwise detectable.

Also to be carefully controlled is the speed of the surface being inspected, and the distance of the cameras from the heat source. Depending upon the thickness of the material and its thermal diffusivity, the thermal transient results in a change in the rate of temperature change. This "pulse" will reflect upon the rear surface of the material and return to the front surface as a secondary heat peak. Such a peak will contain magnified information regarding flaws and the like which may be analyzed against the previous transmissive data to determine the precise location of flaws.

The images may be acquired to a database and displayed by appropriate software, e.g. EchoTherm™ Software, from Thermal Wave Imaging, Inc. Lathrup Village, Mich.; AnalyzIR™ software from FLIR Systems, Portland, Oreg.; or Dynamite™ real-time digital image storage software from Inframetrics, North Billerica, Mass.

Once a thermally acceptable image is established in an appropriate database, a neural network, e.g. Matlab™ Neural Network Toolbox™, fabricated by Math Works, Inc., Natick, Mass., or the Aegis Control™ Neural Network Software, fabricated by Neural Applications Corporation, Coralville Iowa., which is capable of learning repetitive pattern imaging (image recognition) may analyze the recorded pulse for acceptability criterion.

Thus, optimally, the material will be traveling at such a speed such that the first set of sensor cameras will image a transmissive thermal pulse, while the second pair of camera sensors will image an internally reflected thermal pulse.

Figure 3:
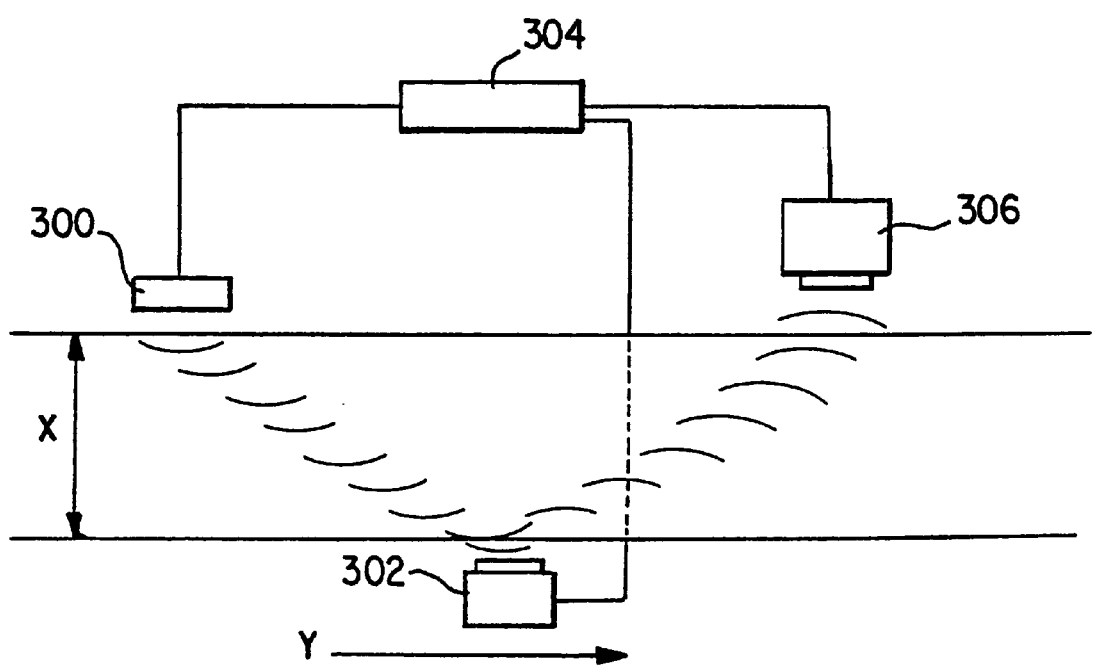
FIG. 3 is a side view of a material being inspected with transient thermal imaging according to the present invention.

FIG. 3 illustrates such a case. The thermal front is imparted by heat source 300 and travels as the material moves in the direction of single-headed arrow y. The thermal pulse travels through thickness x until it strikes the opposite surface in front of sensor camera 302 which records the thermal image emanating from the bottom of the material and sends it to controller 304. The wave is also partially reflected internally and travels back up to the upper surface, where it causes thermal emissions which are captured by sensor camera 306 and relayed to controller 304.

Various heat sources and types may be used—flash lamps can instantaneously raise the heating profile of the sheet being studied; lasers can scan the surface to provide a path of heating (diode lasers being preferred); conventional high intensity lamps (2000–8000 joules), preferably about 6000 joules; and magnetic induction coils may use the material as a susceptor to impart heat energy.

Figure 5:
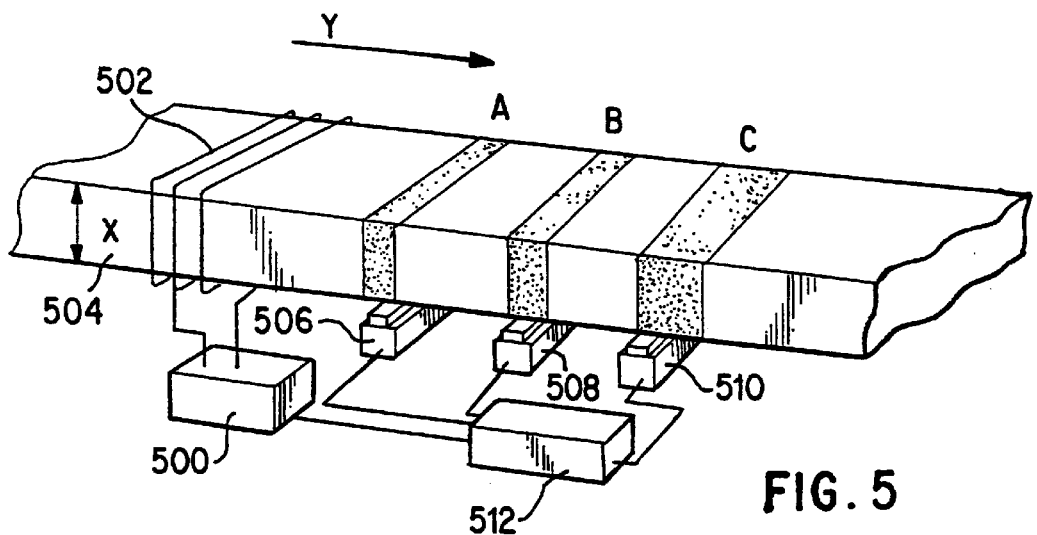
FIG. 5 is a perspective view of an inductively excited imaging system according to the present invention.

A magnetic induction heater for transient thermography is illustrated in FIG. 5. AC current source 500 powers induction coil 502. This imparts thermal energy to the material 504, provided it has sufficient metallic components which will function as a susceptor material to the expanding-contracting magnetic field generated by the induction coil. If the AC current is switched on and off it will create a transient thermal pulse within the material.

As the material travels in the direction of arrow y, the pulse conducts within the material and spreads out. Thermal band A is scanned by camera 506, while thermal band B is scanned by camera 508, and thermal band C is scanned by camera 510. The series of imparted thermal pulses is controlled by controller 512. The scanned images are also fed into controller 512 where they undergo image analysis to determine the presence or absence of flaws.

The novel inspection and control system of the present application has combined an effective thermal detection sensitivity with a predetermined stimulus impulse geometry and power profile to detect flaws, and consequently adjust the optimum system processing parameters for the manufacture of the sheet materials. Flaw location may also be "marked" to save on waste material, allowing for early removal of the material from the process control by excision by cutting. Excision may also consisdt of mere marking with a marker to indicate the material is not to be processed.

Figure 4:
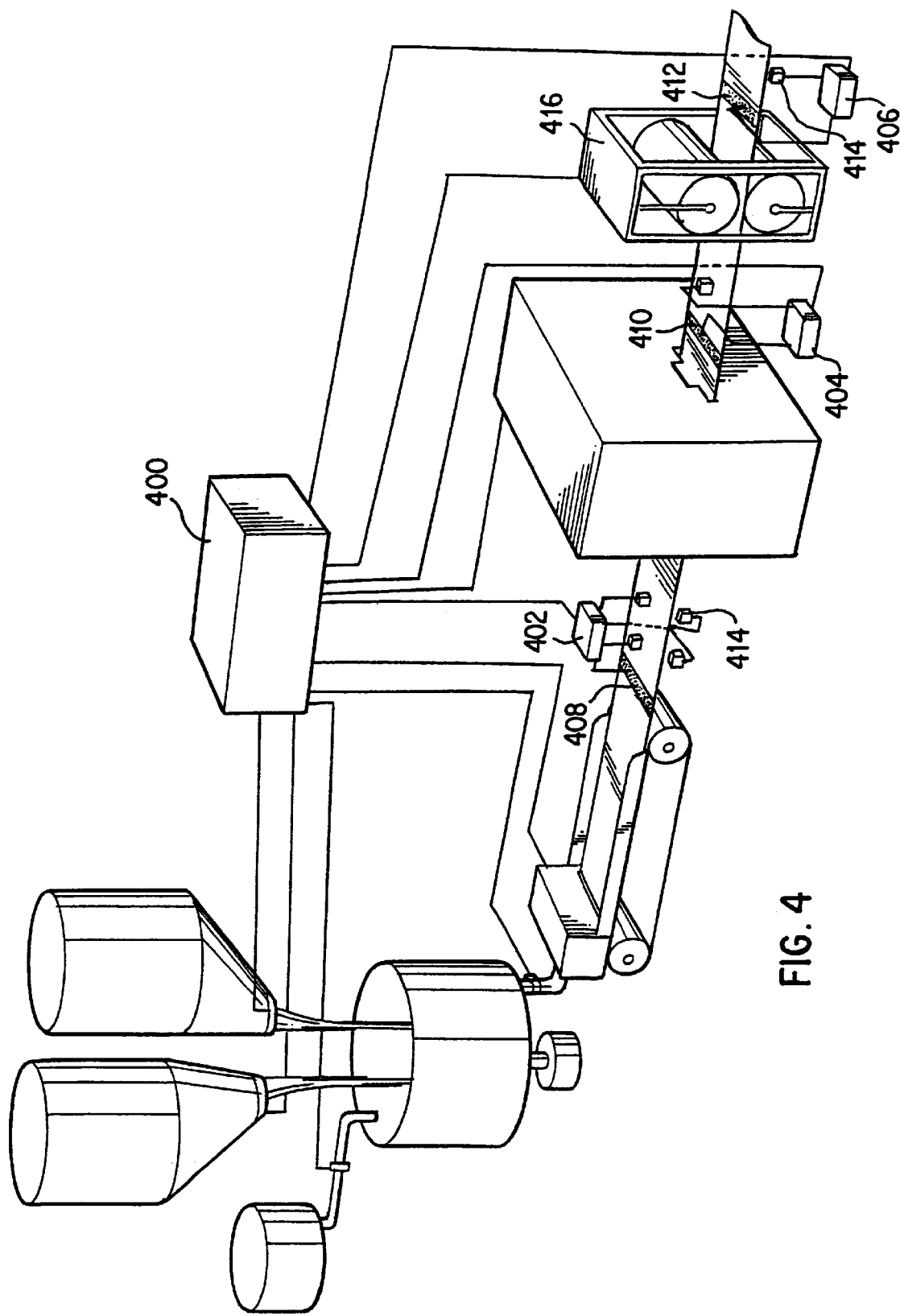
FIG. 4 is a perspective view of a production line for the manufacture of an alloy according to the present invention with a preferred arrangement of inspection and feedback control.

Turning now to FIG. 4, it may be seen that such a system of inspection is placed in strategic locations in a manufacturing facility and integrated into the overall process control. Central controller 400 controls the overall functioning of the process, including regulating materials flow, thickness, speed of the conveyor, drying temperature, vacuum pressure and roller compaction pressure.

Inspection controllers 402, 404, and 406 are strategically placed immediately after various processing steps. Each inspection station is equipped with a respective heating means 408, 410, 412 for imparting a thermal pulse or thermal energy. The inspection stations then have paired or singular camera sensors 414 for inspecting the surface of the material.

Importantly, each of the inspection controllers is linked to the central controller and provides image analysis feedback to the controller. For example, if controller 412 indicates the density is right, but the thickness is wrong, the pressure on roll compactor 416 may be adjusted, and/or the orifice of the head box where the tape casting is extruded onto the conveyor adjusted to increase or decrease the thickness while maintaining the density.

Once the material has been excited thermally, several physics principles come into play. First, the thermal response of the material is a function of the thickness of the material. Second, the thermal response of the material is a function of its thermal diffusivity. Third, the thermal diffusivity of the material is affected by its constituent makeup and physical characteristics. Variations in local thermal properties can now be spatially correlated to defects such as cracks, inclusions, voids, disbonds, and other interruptions of uniformity.

An important part of the present invention includes the identification and calculation of appropriate relationships when dealing with thermal impulse transmissivity. Not wishing to be bound by theory, applicants currently understand the principles involved to be as follows.

In a materials environment, the thermal transient time under impulse heating is calculated by the following known equation:

$$k\nabla^2 T = \rho C \partial T/\partial t \qquad (I)$$

where $\rho$=density; k=thermal conductivity, T=temperature, and C=specific heat. This holds true for the heat transfer of an isotropic homogeneous material.

This thermal transient time, of this material derives, in part, from the thermal diffusivity ($\alpha$), which is represented by the following:

$$\alpha = \frac{k}{\rho C_p}. \qquad (II)$$

These relationships may be relied upon to predict a thermal field. Variations from this solution may be used to determine variations in the underlying material.

As we are interested in calculating the peak thermal impulse arrival time as a function of the thickness of the material being analyzed, we define it as the time for the arrival of the peak arrive at depth x. The second peak arrives when the reflected thermally diffused wave arrives at such depth point x. This reflection is from the back wall of the sample.

The techniques of transmissive and reflective thermography yield a key theoretical result, namely the relationship:

$$t_c \propto \frac{L^2 \cdot \rho \cdot C}{k} \qquad \text{(III)}$$

indicating that characteristic time constants ($t_c$) are fundamentally related (proportional) to sheet properties of thickness (L), density, thermal conductivity, and specific heat.

Establishing baseline values of each for the "ideal" product of manufacture in a database lookup table, or through preset gate values, enables a process central controller to determine when the values have strayed from the ideal and to manipulate an aspect of the production process, or a plurality of aspects of the production process to bring the values into acceptable limits. Such a database is established through a plurality of runs and subsequent analysis, but will be dependent on the material being processed and its desired parameters.

Figure 6A:
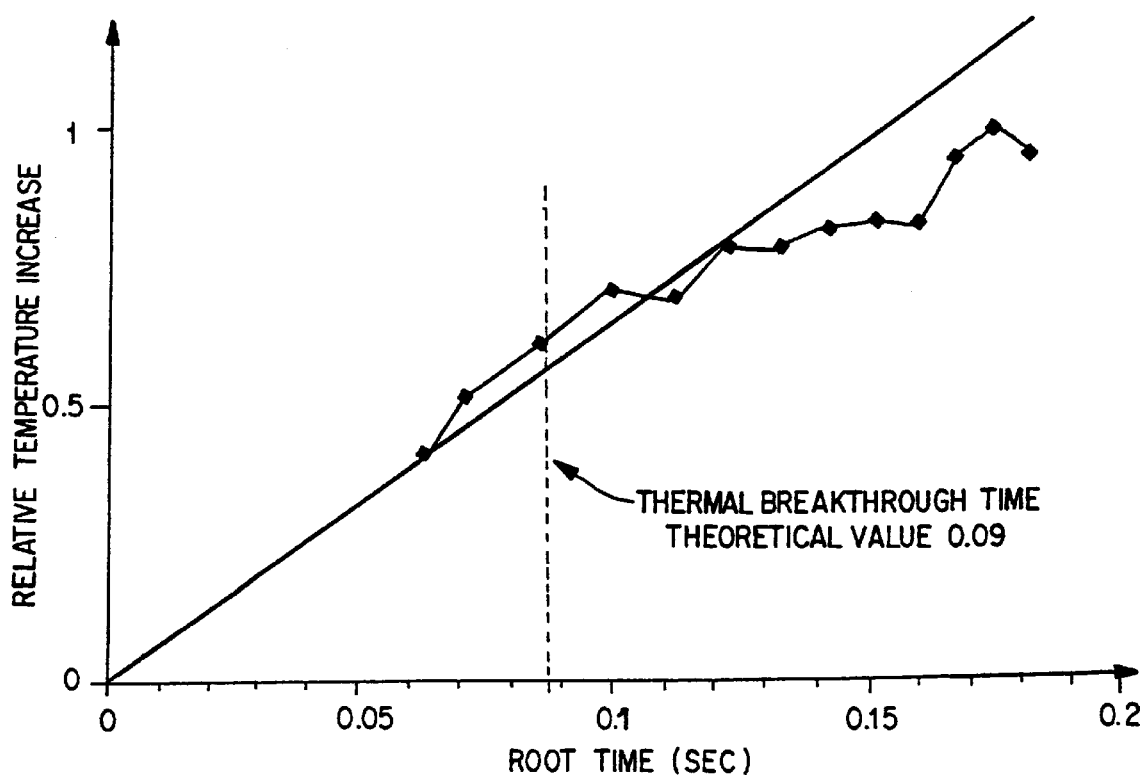
FIG. 6A is a graphical representation of the relative thermal increase versus the square root of time (root time).

FIG. 6A graphically illustrates the concepts discussed above. For a material being analyzed by thermal transmission, the surface scanned relative temperature increase can be predicted based upon the calculated theoretical thermal breakthrough time. Variances from that plot indicate irregularities.

Figure 6B:
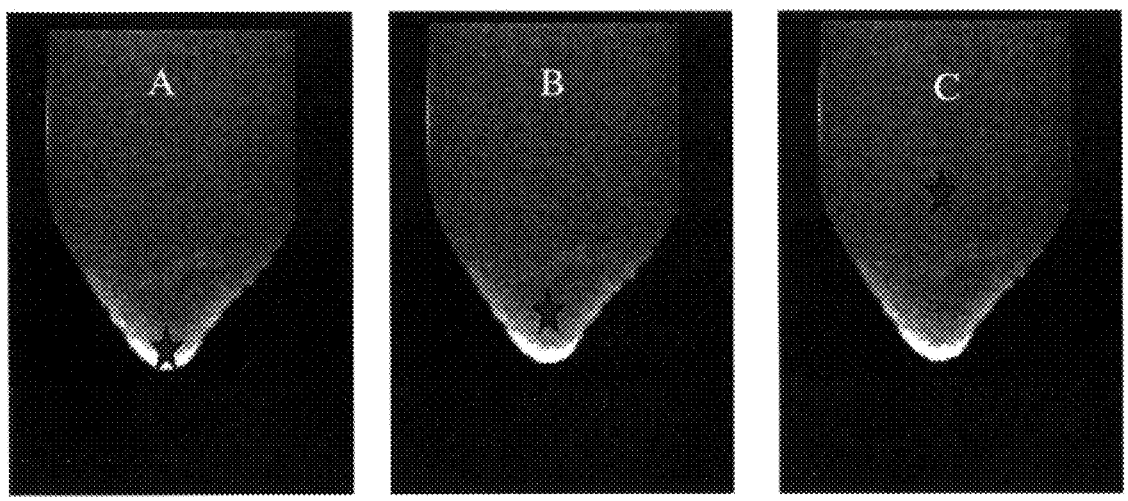
FIG. 6B is a triplicate image of a transmission imaged sample showing various sampling locations.

A specific case is illustrated in FIG. 6B, where a tapered sample of an iron aluminide green sheet having a thickness ranging from 0.013 inch to 0.026 inch was heated on the opposite side of the image collection device (thermal transmissivity). In the image designated A, the sampling location is almost at the tip; in the image designated B the sampling location is further towards the interior, and in the image designated C, the sampling location is central.

Figure 6C:
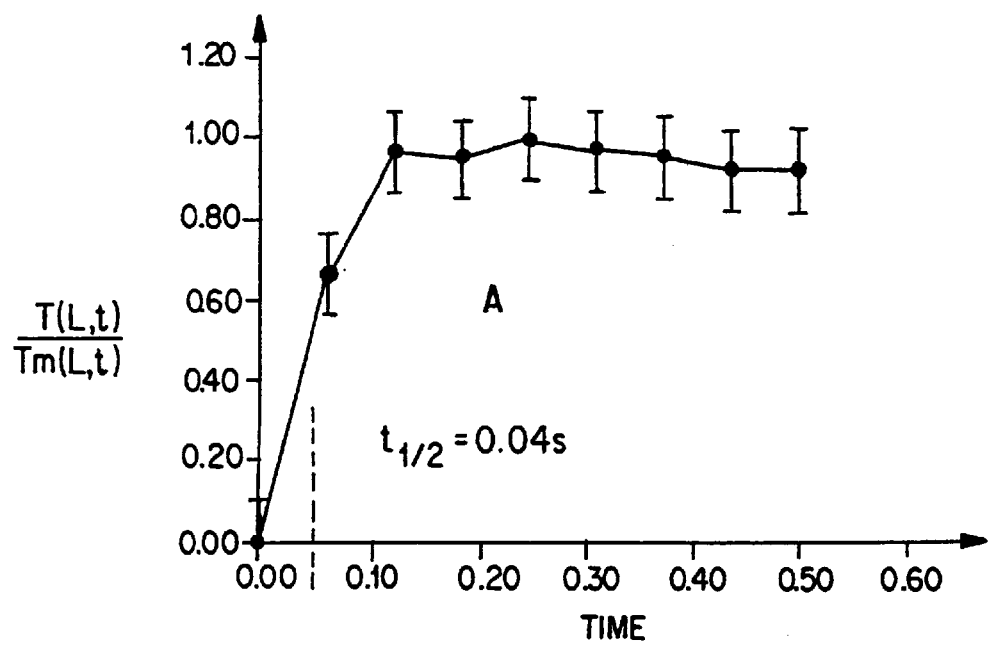
FIG. 6C is a graphical representation of the relative temperature change as a function of time at position A of FIG. 6B.
Figure 6D:
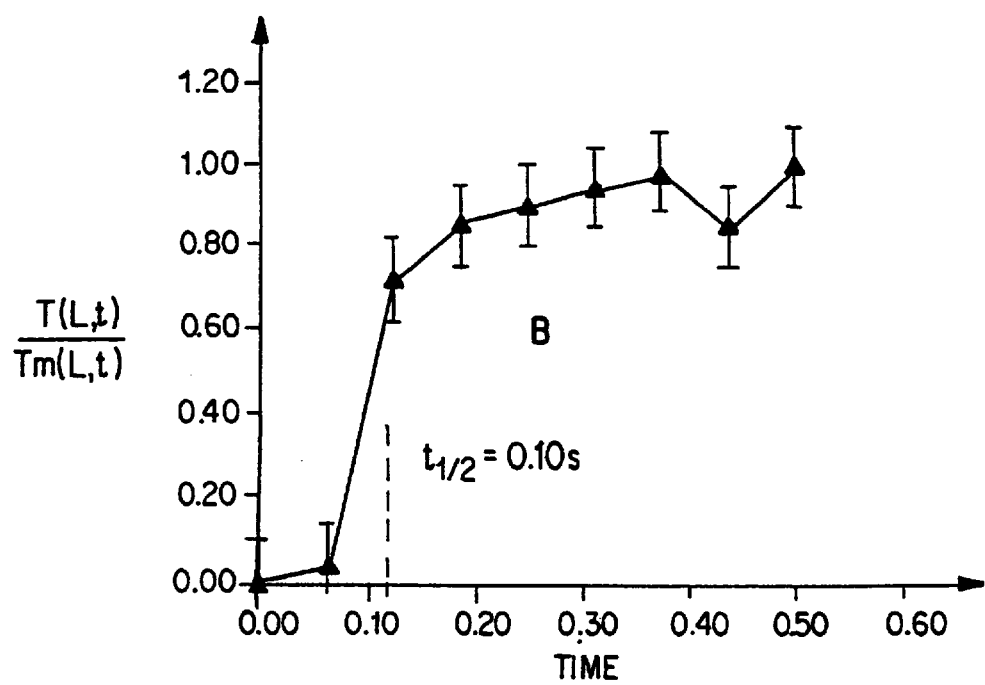
FIG. 6D is a graphical representation of the relative temperature change as a function of time at position B of FIG. 6B.
Figure 6E:
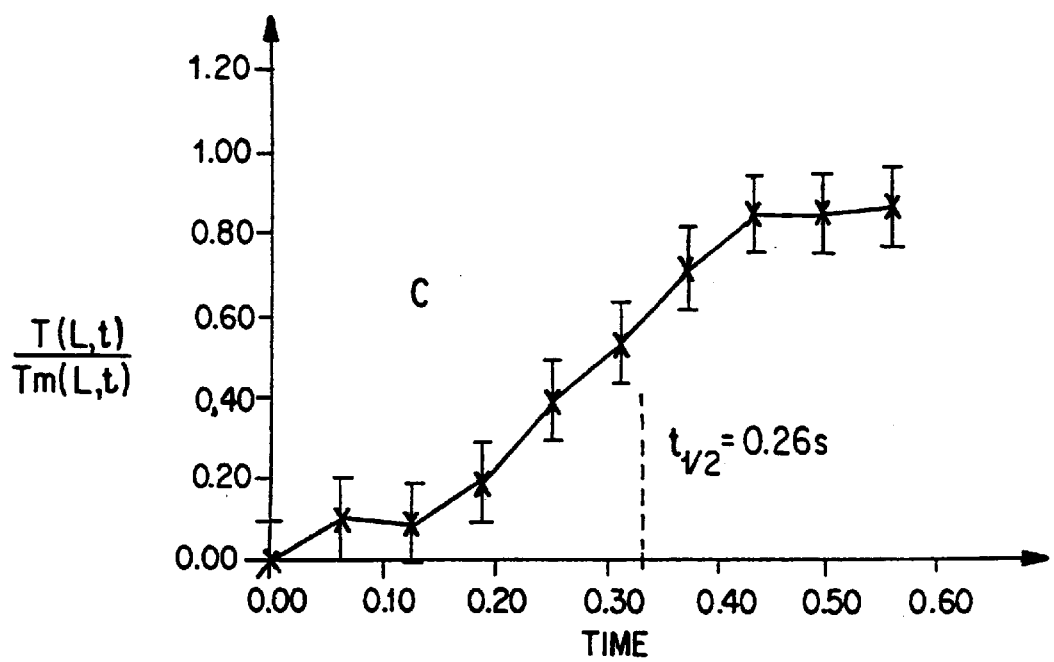
FIG. 6E is a graphical representation of the relative temperature change as a function of time at position C of FIG. 6B.

Turning now to FIGS. 6C, 6D, and 6E, plotted as a function of time (x axis) versus instantaneous temperature, characteristic curves are developed. Plainly, A differs from B which differs from C. Data analysis will tell one exactly how. For example, the t½ times may be quantified as A=0.04, B=0.10, and C=0.26, which may be directly correlated to thickness, density, specific heat, and thermal conductivity. As may be seen from equation III, once three parameters are known, the last may be calculated and compared to the independently measured value.

In an especially preferred embodiment, a 6 kilojoule flashlamp is used as the illumination source. The camera is set to a line scan instead of full frame scan, allowing for a 12 kHz scan time with 30 lines being scanned.

Figure 6F:
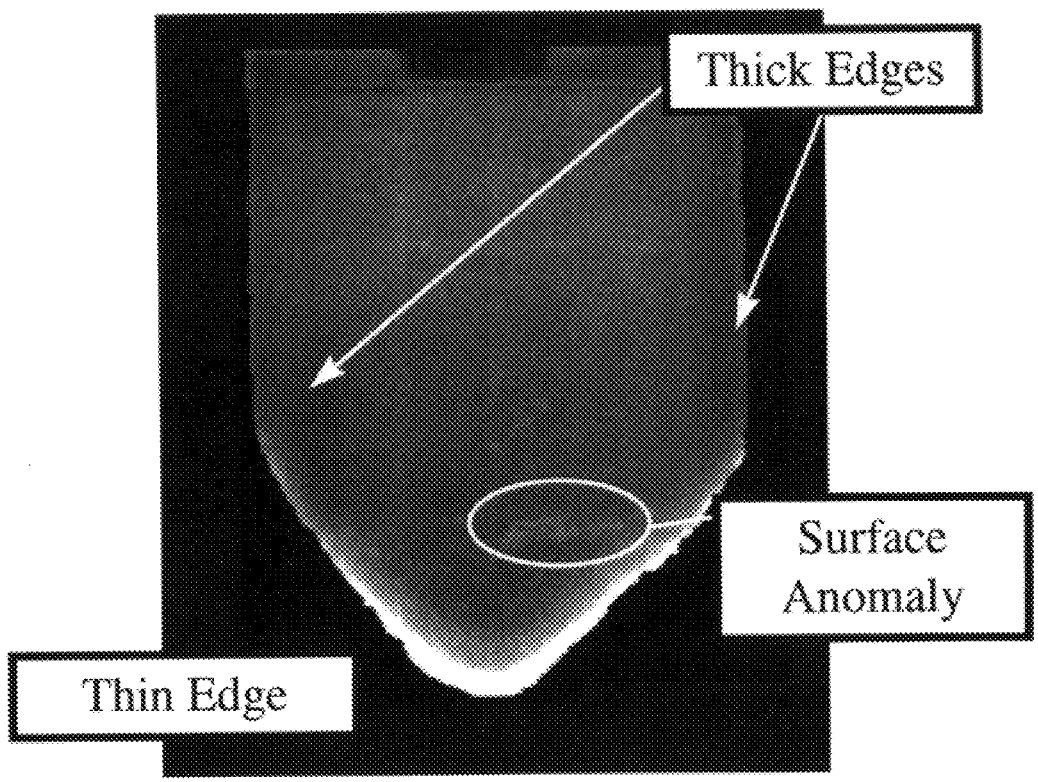
FIG. 6F is a reflectance image according to the present invention.

Given space considerations in processing plants, a preferred embodiment of the present invention has all of the imaging equipment on a single side of the material being analyzed. FIG. 6F illustrates such an image obtained by external reflective imaging, 0.167 seconds after step heating, where the heat is being constantly applied. Flaws become readily apparent.

One embodiment of the present invention which increases its data collection ability is as follows. One surface (usually the upper) is bombarded with high intensity photons beginning at a very precise point. The shadow, i.e. the delay time it takes for the wave front to get to the other surface provides a very accurate measurement of the thickness of the sample being analyzed. Simultaneously, immediately thereafter, or in parallel, thermal pulses from another source may be imparted to measure density and inspect for flaws. The simultaneous acquisition of both data pieces enables the density and thickness to be calculated separately.

Figure 7:
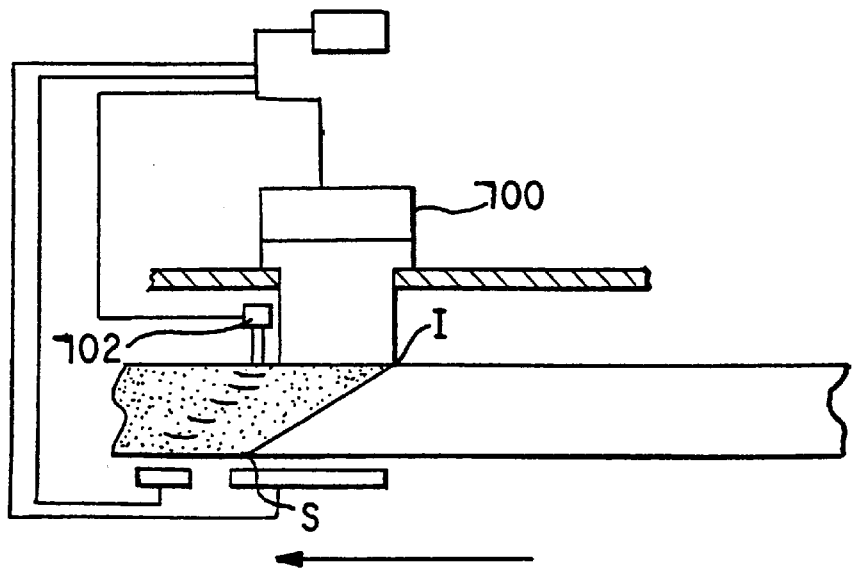
FIG. 7 is a side view of a preferred embodiment of the thermal imaging system of the present invention.

Turning now to FIG. 7, the dual inspection system of the preferred embodiment of the present invention is illustrated. A photonic or other illumination source 700 impinges upon the surface of the material at point I. The "shadow" effect of the material causes a delay in the radiation travel to point S. The duration of this travel, and the manner in which the wave arrives gives important analytical data as to the density, uniformity, and thickness of the material. It also establishes a baseline through which thermal impulses from second illumination source 702 travel. The data may then be statistically analyzed to separate out the density and thickness data.

Suitable instrumentation for receiving the thermal images from the surface of the material and associated equipment include the THERMOPROFILE® 6 LT Infrared Line Scanner, available from Agema Infrared Systems, Inc.

Figure 8:
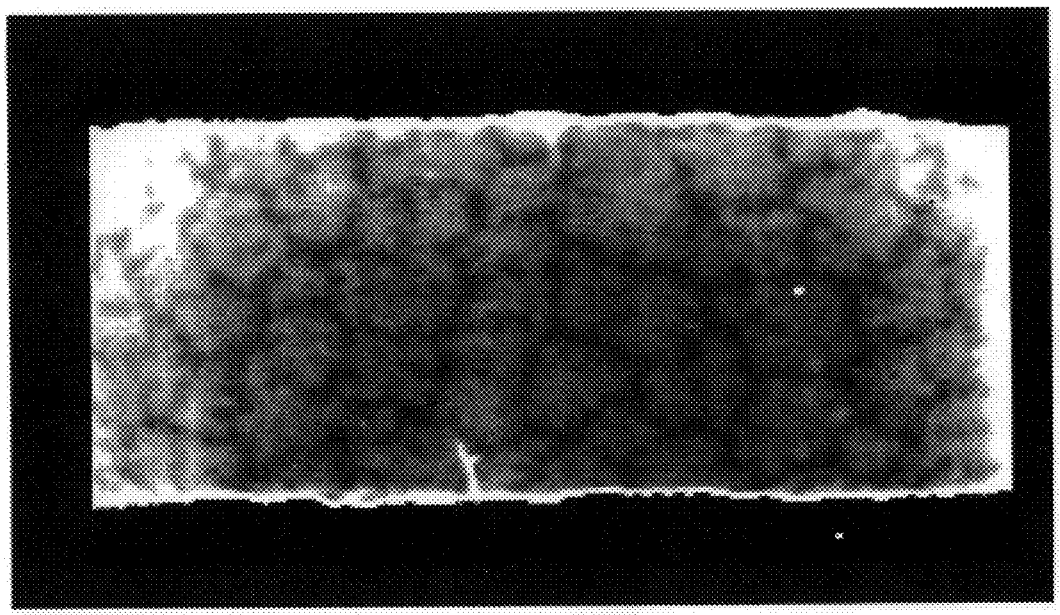
FIG. 8 is a reflectance image (of a tape cast sample) according to the present invention.

FIG. 8 is a digital image of a tape cast sample 0.010 seconds after a front flash. The loose structure is clearly visible with denser regions surrounded by cracks.

Figure 9:
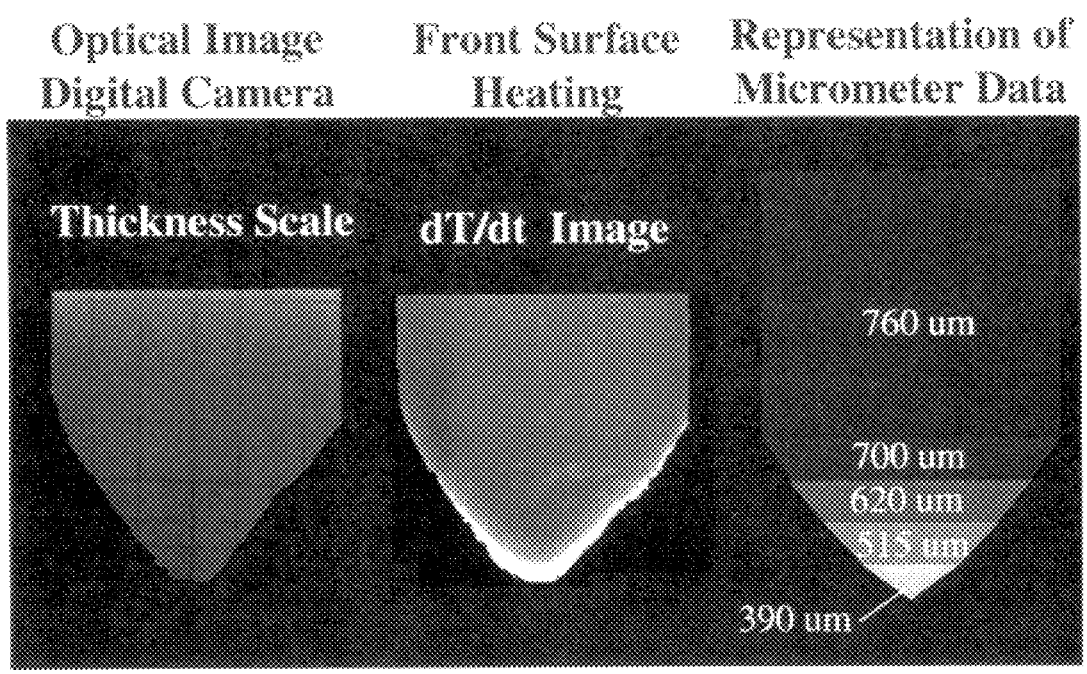
FIG. 9 is a digital illustration comparing optical, thermal, and physical measurement data.

FIG. 9 compares an optical inspection with a transient thermography image and a physical measurement of the specimen. The thermography image glows brighter in the thinner regions where the photon flux from the surface is greater than the remainder of the sample.

Figure 10:
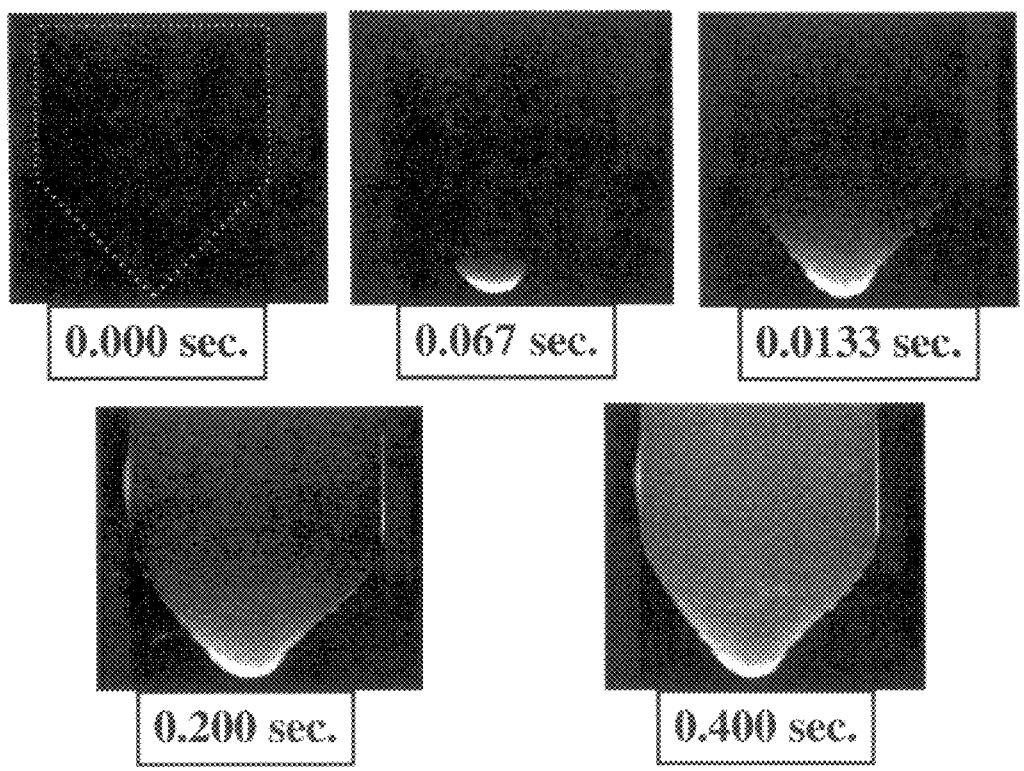
FIG. 10 is a digital image of, in time sequence, of thermal transmissive images according to the present invention.

FIG. 10 is an example of transmittal thermography illustrating a time lapse series of images where a tapered sample becomes clearly evident. The thinnest portions become visible in a faster manner, and they remain brighter for a period of time.

Figure 11:
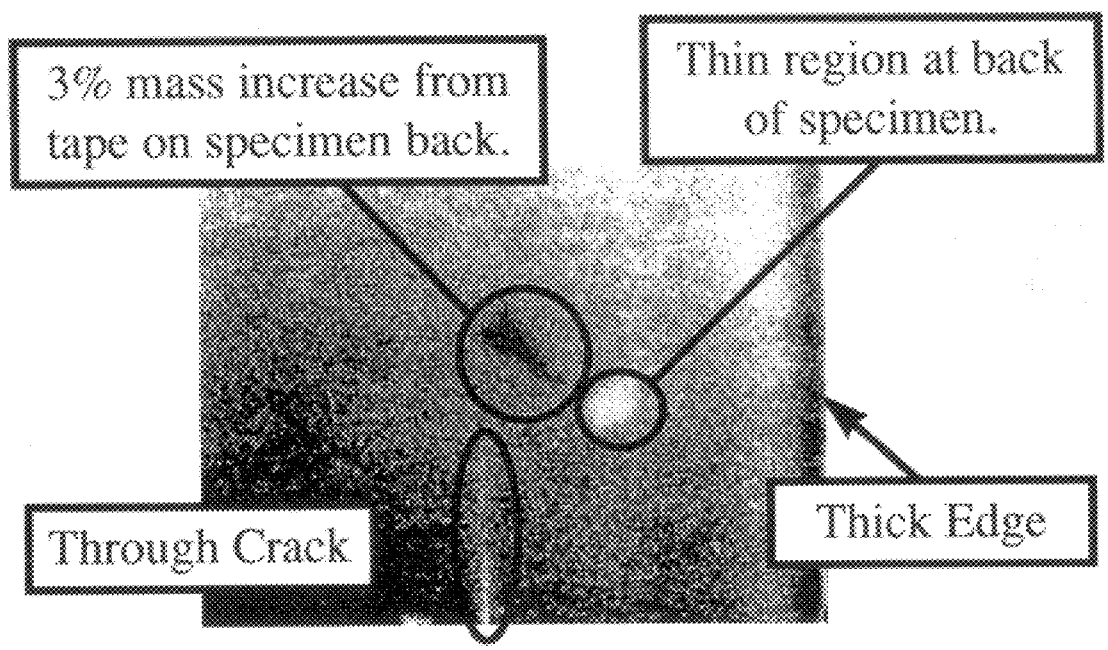
FIG. 11 is a digital image of a sample containing defects, imaged by reflectance according to the present invention.

FIG. 11 is an example of transient thermography's ability to spot a multitude of defects, including excess mass, thin regions, cracks, and edge deformities.

In a preferred embodiment, the defect region is registered and identified for removal from the process flow. It may be marked automatically with a visible indicator, or the process controller may register and automatically remove the production portion from the stream by physical excision.

This invention is especially preferred for sheet material having a thickness dimension much smaller than its width or length, wherein for purposes of the sample and diffusion, it is essentially one-dimensional.

The invention having been described above, I claim:

I claim:

1. An apparatus for inspecting a sheet material produced by a production process having a process flow, comprising:
   a central process controller configured to control at least one aspect of the production process,
   a source of incident radiation which impinges upon the sheet material;
   a conveyor for moving the sheet material in a single plane;
   a plurality of infrared detectors located proximate to a surface of the sheet material, said infrared detectors positioned such that they can create an image of the surface of the sheet material at or downstream of the source of incident radiation; wherein there is an infrared detector positioned to receive transmitted pulsed radiation, and an infrared detector positioned to receive transmitted unpulsed radiation,
   a computer which is in communication with the central process controller and configured to
      receive and analyze the image from the infrared detector to determine physical characteristics of the sheet material, and
      transmit the determined physical characteristics to the central process controller;
   whereby the central process controller adjusts the at least one aspect of the production process in response to the determined physical characteristic.

2. An apparatus as claimed in claim 1, further comprising an index device for locating an inspected portion of the sheet material.

3. An apparatus as claimed in claim 2, further comprising an excisor to remove an inspected portion of the sheet material from the process flow.

4. An apparatus as claimed in claim 1, wherein there is an infrared detector positioned to receive the externally reflected radiation.

5. An apparatus as claimed in claim 1, wherein there is an infrared detector positioned to receive the internally reflected radiation.

6. An apparatus as claimed in claim 1, wherein the infrared detectors generate data which is compared to separate density and thickness information.

7. An apparatus as claimed in claim 1, wherein the source of incident radiation is a lamp generating light selected from the group consisting of visible light, infrared light, and ultraviolet light.

8. An apparatus as claimed in claim 1, wherein the source of incident radiation is inductive.

9. An apparatus as claimed in claim 1, wherein the source of incident radiation is a laser.

10. An apparatus as claimed in claim 1, wherein the source of incident radiation puts out between 2,000 and 8,000 joules.

11. An apparatus as claimed in claim 1, wherein the source of incident radiation puts out about 6,000 joules.

12. An apparatus as claimed in claim 1, wherein there are a plurality of infrared detectors positioned downstream from the source of incident radiation, and the sheet material is translated at such a rate as to give time-differentiated images of the same portion of the surface imaged in each camera.

13. A method as claimed in claim 1, wherein the step of analyzing comprises training a neural network to recognize acceptable thermal signatures.

14. An apparatus as claimed in claim 1, wherein there are a plurality of sources of incident radiation, one of which is pulsed.

15. An apparatus as claimed in claim 14, wherein said plurality of sources of incident radiation impinge on the same location.

* * * * *